US010922875B2

(12) United States Patent
Lee et al.

(10) Patent No.: US 10,922,875 B2
(45) Date of Patent: Feb. 16, 2021

(54) ULTRASOUND SYSTEM AND METHOD OF DISPLAYING THREE-DIMENSIONAL (3D) IMAGE

(71) Applicant: SAMSUNG MEDISON CO., LTD., Hongcheon-gun (KR)

(72) Inventors: Jin-yong Lee, Hongcheon-gun (KR); Sung-wook Park, Hongcheon-gun (KR); Jin-ki Park, Hongcheon-gun (KR); Joo-hyun Song, Hongcheon-gun (KR); Bong-heon Lee, Hongcheon-gun (KR)

(73) Assignee: SAMSUNG MEDISON CO., LTD., Hongcheon-gun (KR)

( * ) Notice: Subject to any disclaimer, the term of this patent is extended or adjusted under 35 U.S.C. 154(b) by 1315 days.

(21) Appl. No.: 14/929,590

(22) Filed: Nov. 2, 2015

(65) Prior Publication Data

US 2016/0125641 A1 May 5, 2016

(30) Foreign Application Priority Data

Oct. 31, 2014 (KR) .......................... 10-2014-0150637

(51) Int. Cl.
*A61B 8/00* (2006.01)
*G06T 15/20* (2011.01)
(Continued)

(52) U.S. Cl.
CPC .............. *G06T 15/20* (2013.01); *A61B 8/464* (2013.01); *A61B 8/465* (2013.01); *A61B 8/466* (2013.01);
(Continued)

(58) Field of Classification Search
CPC ......... A61B 8/464; A61B 8/465; A61B 8/466; A61B 8/483; A61B 8/523; A61B 8/4245;
(Continued)

(56) References Cited

U.S. PATENT DOCUMENTS 5,926,165 A * 7/1999 Grewer .................... H04N 5/45
348/E5.112
7,801,351 B2 9/2010 Srinivas et al.
(Continued)

FOREIGN PATENT DOCUMENTS

JP 2007-136209 A 6/2007
JP 2011161031 A 8/2011
(Continued)

OTHER PUBLICATIONS

Communication dated Mar. 24, 2016, issued by the European Patent Office in counterpart European Application No. 15156853.2.

*Primary Examiner* — Baisakhi Roy
(74) *Attorney, Agent, or Firm* — Sughrue Mion, PLLC

(57) ABSTRACT

Provided is an ultrasound system and an image display method of displaying an ultrasound image on an auxiliary display. The ultrasound system generates a three-dimensional (3D) image in a first orientation with respect to ultrasound volume data acquired from an object and displays the 3D image in the first orientation on a display. The ultrasound system also acquires position information and orientation information of an auxiliary display and determines a second orientation based on the acquired position information and orientation information. The ultrasound system then generates a 3D image in the determined second orientation and controls the 3D image in the second orientation to be displayed on the auxiliary display.

24 Claims, 11 Drawing Sheets

(51) Int. Cl.
  *G06F 3/0346* (2013.01)
  *G09G 5/00* (2006.01)
  *A61B 8/08* (2006.01)
  *G06T 7/70* (2017.01)
  *G06F 3/0481* (2013.01)
  *G06F 3/01* (2006.01)

(52) U.S. Cl.
  CPC .............. *A61B 8/483* (2013.01); *A61B 8/523* (2013.01); *G06F 3/011* (2013.01); *G06F 3/0346* (2013.01); *G06F 3/04815* (2013.01); *G06T 7/70* (2017.01); *G09G 5/003* (2013.01); *A61B 8/565* (2013.01); *G06T 2210/41* (2013.01)

(58) Field of Classification Search
  CPC ...... A61B 1/00193; A61B 2017/00203; A61B 2090/365; A61B 2090/378; A61B 17/3403; A61B 8/0841; A61B 8/14; A61B 8/462
  See application file for complete search history.

(56) References Cited

U.S. PATENT DOCUMENTS

| | | | |
|---|---|---|---|
| 10,477,191 B2* | 11/2019 | Kuribayashi | G09G 3/003 |
| 2009/0003665 A1 | 1/2009 | Berg et al. | |
| 2009/0187102 A1* | 7/2009 | Di Marco | A61B 8/14 |
| | | | 600/437 |
| 2010/0179428 A1* | 7/2010 | Pedersen | A61B 8/00 |
| | | | 600/443 |
| 2011/0166451 A1 | 7/2011 | Blaivas et al. | |
| 2013/0197357 A1* | 8/2013 | Green | A61B 8/0841 |
| | | | 600/424 |
| 2013/0342524 A1 | 12/2013 | Kotian et al. | |
| 2015/0018683 A1* | 1/2015 | Kwon | A61B 8/0833 |
| | | | 600/443 |
| 2015/0206339 A1* | 7/2015 | Chun | G06T 15/205 |
| | | | 345/419 |
| 2016/0220324 A1* | 8/2016 | Tesar | G02B 21/0012 |

FOREIGN PATENT DOCUMENTS

| | | |
|---|---|---|
| JP | 2014-033850 A | 2/2014 |
| KR | 10-2014-0038777 A | 3/2014 |

* cited by examiner

FIG. 4
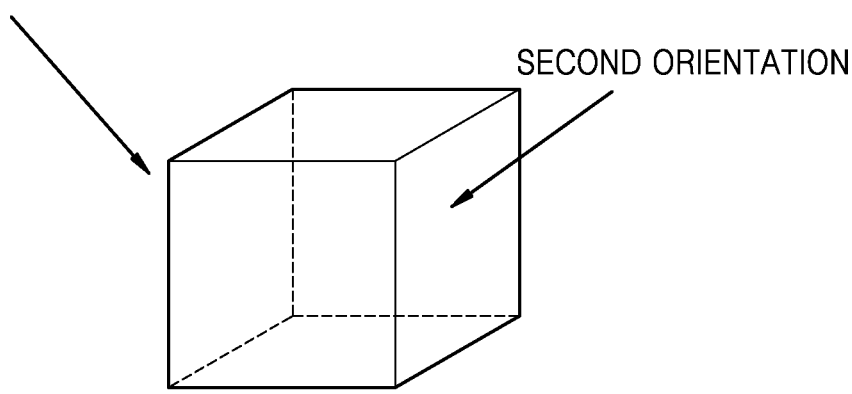
FIRST ORIENTATION
SECOND ORIENTATION
410
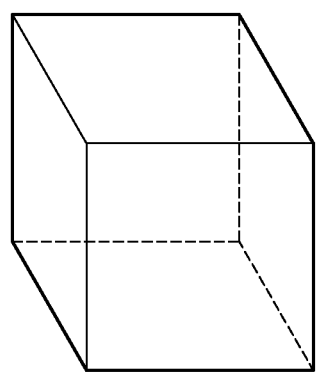
420
FIRST ORIENTATION
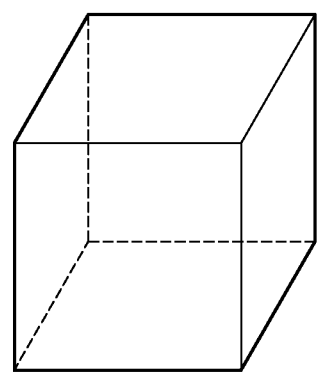
430
SECOND ORIENTATION

FIG. 5B
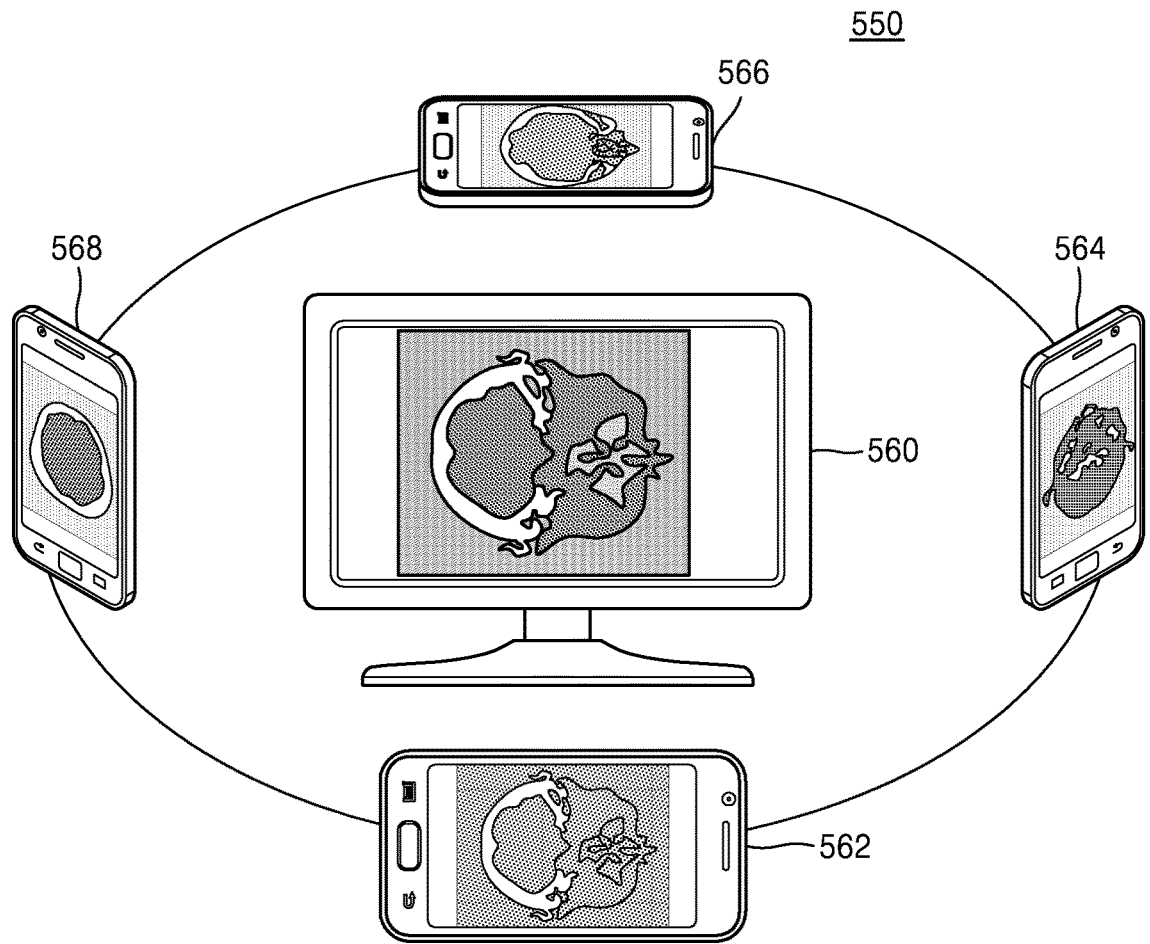
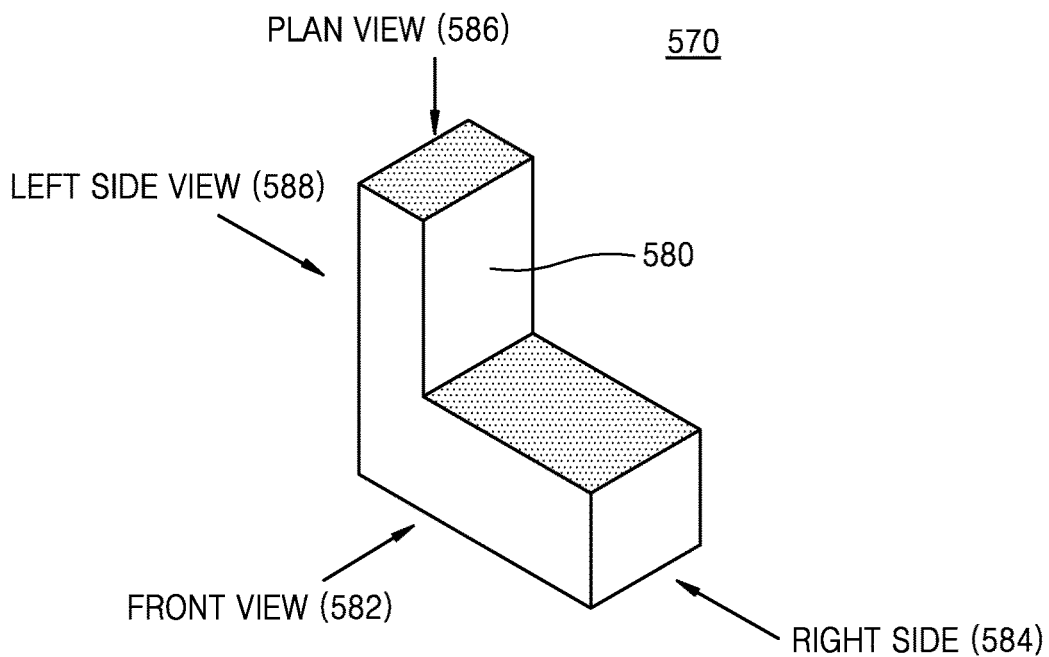

ULTRASOUND SYSTEM AND METHOD OF DISPLAYING THREE-DIMENSIONAL (3D) IMAGE

RELATED APPLICATION

This application claims the benefit of Korean Patent Application No. 10-2014-0150637, filed on Oct. 31, 2014, in the Korean Intellectual Property Office, the disclosure of which is incorporated herein in its entirety by reference.

BACKGROUND

1. Field

One or more exemplary embodiments relate to an ultrasound system and method of displaying an ultrasound image, and more particularly, to an ultrasound system for further intuitively displaying a three-dimensional (3D) ultrasound image by using an auxiliary display.

2. Description of the Related Art

An ultrasound diagnosis device transmits ultrasound signals generated by transducers of a probe to an object and receives echo signals reflected from the object, thereby obtaining images of the interior of the object. In particular, an ultrasound diagnosis device may be used for various medical purposes such as observation of the inside of an object, detection of foreign substances, and assessment of injuries. Such an ultrasound diagnosis device may display information regarding an object in real-time. Furthermore, there is no risk of radioactivity exposure using an ultrasound diagnosis device, unlike in the use of an X-ray diagnosis apparatus, and thus, the ultrasound diagnosis device is very safe. Therefore, an ultrasound diagnosis device is widely used together with other types of imaging diagnosis devices.

In addition, an ultrasound system may display a 3D image of an organ of a human body. In this case, while viewing a 3D image of the organ in one direction, a user needs to view another 3D image of the organ at a different angle. In particular, if a user is able to simultaneously view images of an object in different orientations, the user may acquire more accurate information of the object. For example, during a heart valve crop surgery, a user may perform the surgery with higher accuracy by observing images obtained at different angles at one time.

Various conventional methods of displaying a 3D image at different angles have been proposed. However, according to the methods, it is not only inconvenient to set an angle for rendering at different angles but also requires a long time to display images obtained from different angles according to the set angle.

For example, referring to FIG. 1, four cross-sections 112, 114, 116, and 118 are set for a volume 110 generated based on ultrasound volume data, and ultrasound images 122, 124, 126, and 128 respectively corresponding to the four cross-sections 112, 114, 116, and 118 are displayed. In this case, a user has to preset a position and an angle of a desired cross-section. To do so, the user needs to directly input the position and the angle of the desired cross-section to an ultrasound system and adjust the same.

FIG. 2 illustrates simultaneous displaying of images 212, 214, 216, and 218 taken at different angles for ultrasound volume data. For example, referring to FIGS. 1 and 2, ultrasound images 212 and 214 may be displayed when the cross-sections 112 and 114 of the volume 110 are viewed from the front, respectively. However, even in this case, a user is inconvenienced in having to preset positions and angles of the cross-sections 112, 114, 116, and 118 to be viewed. In particular, if the user desires to view an object at different angles in real-time during a surgical procedure by using an ultrasound system, he or she may suffer more inconvenience under a conventional ultrasound system.

SUMMARY

One or more exemplary embodiments include an ultrasound system and method for intuitively displaying a three-dimensional (3D) ultrasound image by using an auxiliary display.

Additional aspects will be set forth in part in the description which follows and, in part, will be apparent from the description, or may be learned by practice of the presented exemplary embodiments.

According to one or more exemplary embodiments, an ultrasound system includes: a controller configured to generate, from ultrasound volume data acquired from an object, a 3D ultrasound image in a first orientation with respect to the ultrasound volume data; and a display configured to display the generated 3D ultrasound image in the first orientation, wherein the controller acquires at least one from among position information and orientation information of an auxiliary display, generates, from the ultrasound volume data, a 3D ultrasound image in a second orientation with respect to the ultrasound volume data based on the acquired at least one from among the position information and orientation information, and controls the 3D ultrasound image in the second orientation to be displayed on the auxiliary display.

The controller may acquire at least one from among changed position information and changed orientation information of the auxiliary display, generates, from the ultrasound volume data, a 3D ultrasound image in a third orientation with respect to the ultrasound volume data based on the acquired at least one from among the changed position information and the changed orientation information, and controls the 3D ultrasound image in the third orientation to be displayed on the auxiliary display.

The ultrasound system may include the auxiliary display.

The ultrasound system may further include a communication interface for receiving the at least one from among the position information and the orientation information from the auxiliary display. The controller may control the communication interface to transmit the 3D ultrasound image in the second orientation generated based on the received at least one from among the position information and the orientation information to the auxiliary display.

The controller may initialize the at least one from among the position information and the orientation information of the auxiliary display.

The controller may acquire at least one from among changed position information and changed orientation information of the auxiliary display, compare the at least one from among the changed position information and the changed orientation information with the initialized at least one from among the position information and the orientation information, and change the 3D ultrasound image in the second orientation displayed on the auxiliary display according to a comparison result.

When the changed orientation information indicates that the auxiliary display rotates in a first rotation direction, the controller may control the 3D ultrasound image in the second orientation displayed on the auxiliary display to be rotated in a second rotation direction and be displayed on the auxiliary display.

According to one or more exemplary embodiments, an image display device for displaying an ultrasound image includes: a display configured to display a 3D ultrasound image in a first orientation with respect to ultrasound volume data acquired, based on at least one from among position information and orientation information of the image display device; a sensor configured to detect a change in at least one from among a position and an orientation of the image display device; a controller configured to determine at least one from among changed position information and changed orientation information of the image display device according to a detection result; and a communication interface configured to transmit the determined at least one from among the changed position information and the changed orientation information to an external device and receive a 3D ultrasound image in a second orientation with respect to the ultrasound volume data from the external device, the second orientation being based on the at least one from among the changed position information and the changed orientation information. The controller may control the display to display the received 3D ultrasound image in the second orientation.

The sensor includes at least one from among a gyro sensor, an accelerometer, and a magnetic sensor.

The communication interface may communicate with the external device via at least one from among wireless and wired communication channels, and the image display device may be at least one from among a mobile phone, a smartphone, a tablet PC, an auxiliary monitor, and a portable computer.

The controller may initialize the at least one from among the position information and the orientation information of the image display device according to a command that initializes the at least one from among the position information and the orientation information thereof. The communication interface may transmit the initialized at least one from among the position information and the orientation information to the external device.

When the changed orientation information indicates that the image display device rotates in a first rotation direction, the 3D ultrasound image in the second orientation may be a 3D ultrasound image displayed by rotating the 3D ultrasound image with the first orientation in a second rotation direction.

According to one or more exemplary embodiments, a method of displaying an image in an ultrasound system includes: generating, from ultrasound volume data acquired from an object, a 3D ultrasound image in a first orientation with respect to the ultrasound volume data; displaying the generated 3D ultrasound image in the first orientation; acquiring at least one from among position information and orientation information of an auxiliary display; generating, from the ultrasound volume data, a 3D ultrasound image in a second orientation based on the acquired at least one from among the position information and the orientation information; and controlling the 3D ultrasound image in the second orientation to be displayed on the auxiliary display.

According to one or more exemplary embodiments, a method of displaying an image in an image display device includes: displaying a 3D ultrasound image in a first orientation with respect to ultrasound volume data, wherein the first orientation is determined based on at least one from among position information and orientation information of the image display device; detecting a change in at least one from among a position and an orientation of the image display device; determining at least one from among changed position information and changed orientation information of the image display device according to a detection result; transmitting the determined at least one from among the changed position information and the changed orientation information to an external device; receiving a 3D ultrasound image in a second orientation with respect to the ultrasound volume data from the external device, wherein the second orientation is determined based on the at least one from among the changed position information and the changed orientation information; and displaying the received 3D ultrasound image in the second orientation.

BRIEF DESCRIPTION OF THE DRAWINGS

These and/or other aspects will become apparent and more readily appreciated from the following description of the exemplary embodiments, taken in conjunction with the accompanying drawings in which:

FIG. 4 illustrates an example of 3D ultrasound images obtained in different orientations with respect to the same ultrasound volume;

FIGS. 5A and 5B are diagrams illustrating actual implementation of configurations of an ultrasound system according to an exemplary embodiment;

DETAILED DESCRIPTION

Figure 1:
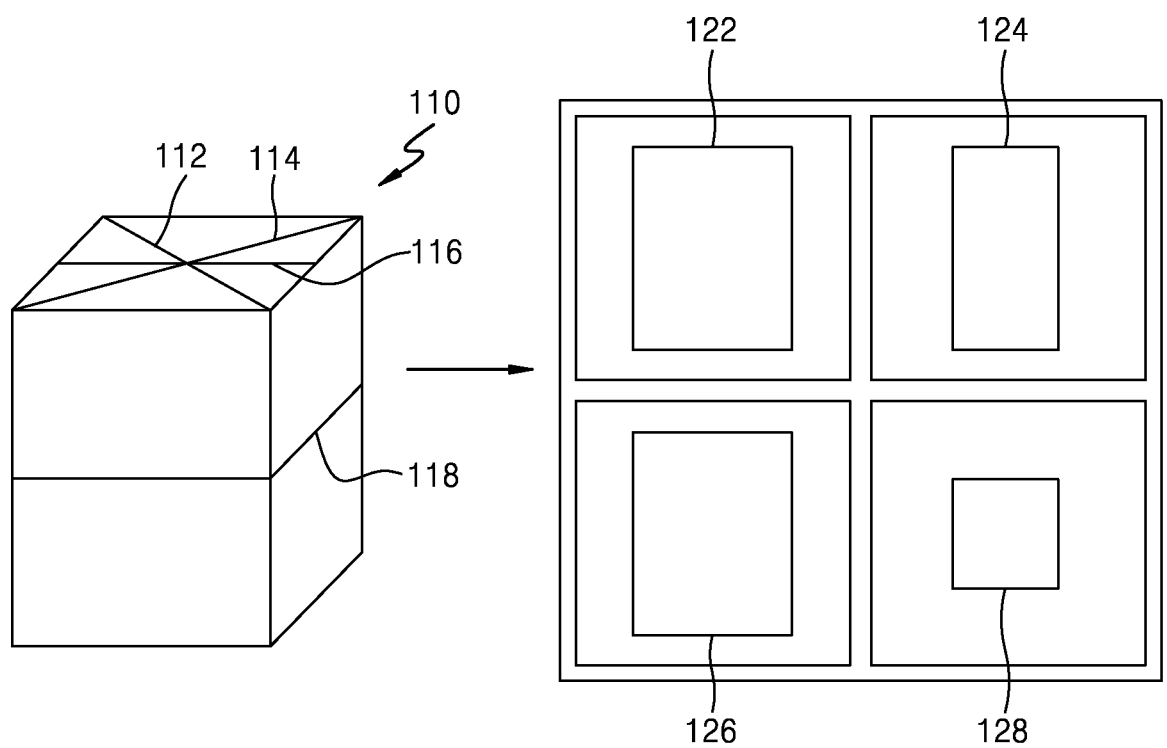
FIG. 1 illustrates an example of displaying a three-dimensional (3D) image.
Figure 2:
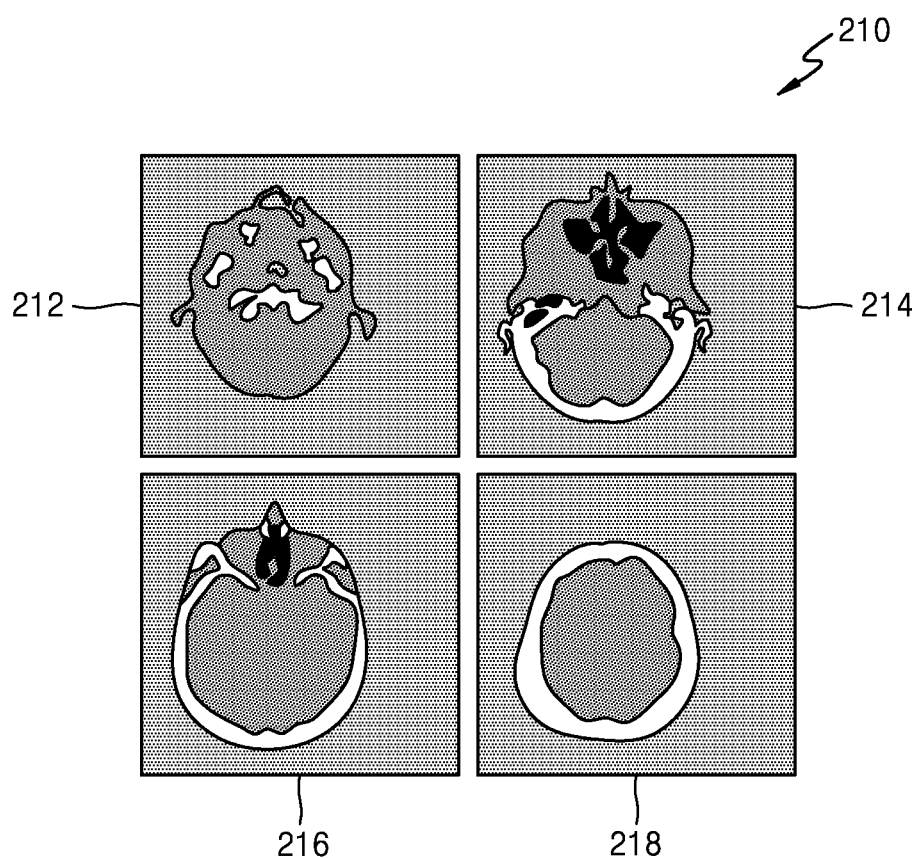
FIG. 2 illustrates another example of displaying a 3D image.

Reference will now be made in detail to exemplary embodiments, examples of which are illustrated in the accompanying drawings, wherein like reference numerals refer to like structural elements throughout. Expressions such as "at least one of," when preceding a list of elements, modify the entire list of elements and do not modify the individual elements of the list.

The terms used in this specification are those general terms currently widely used in the art in consideration of functions in regard to exemplary embodiments, but the terms may vary according to the intention of those of ordinary skill in the art, precedents, or emergence of a new technology in the art. Also, specified terms may be selected by the applicant, and in this case, the detailed meaning thereof will be described in the detailed description of the inventive concept. Thus, the terms used in the specification should be understood not as simple names but based on the meaning of the terms and the overall description of the inventive concept.

Throughout the specification, it will also be understood that when a component "includes" or "comprises" an element, unless there is a particular description contrary thereto, it should be understood that the component can further include other elements, not excluding the other elements. In addition, terms such as " . . . unit", " . . . module", or the like refer to units that perform at least one function or operation, and the units may be implemented as hardware or software or as a combination of hardware and software.

Throughout the specification, an "ultrasound image" refers to an image of an object obtained using an ultrasound wave. Furthermore, in the present specification, an "object" may include a person or an animal, or a part of a person or an animal. For example, the object may include organs such as the liver, the heart, the womb, the brain, a breast, and the abdomen, or a blood vessel. Furthermore, the "object" may include a phantom. The phantom is a material having a volume that is approximately close to the density and effective atomic number of a living organism.

In the present specification, a "user" refers to a medical professional, such as a doctor, a nurse, a medical laboratory technologist, and a medical imaging expert, and a technician who repairs a medical apparatus, but the user is not limited thereto.

Figure 3:
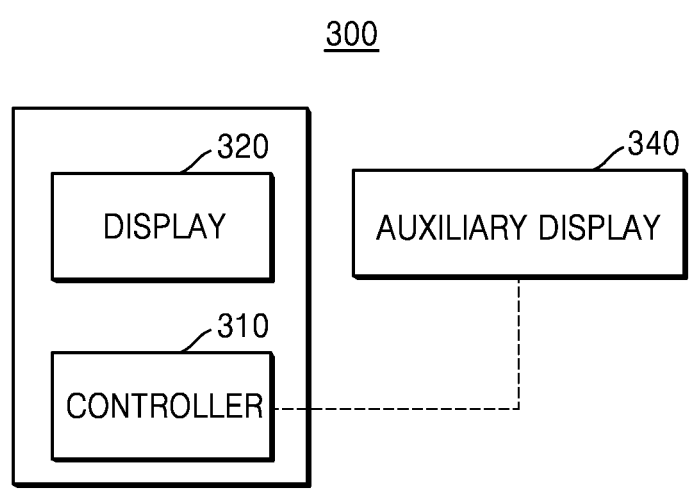
FIG. 3 is a block diagram of an ultrasound system according to an exemplary embodiment.

FIG. 3 is a block diagram of an ultrasound system 300 according to an exemplary embodiment. Referring to FIG. 3, the ultrasound system 300 according to the present exemplary embodiment includes a controller 310 and a display 320.

The controller 320 generates a three-dimensional (3D) ultrasound image based on ultrasound volume data acquired from an object.

According to an exemplary embodiment, the ultrasound volume data may be created based on an ultrasound echo signal received by transmitting an ultrasound signal to an object. In another exemplary embodiment, the ultrasound volume data may be received from an external device. In another exemplary embodiment, the ultrasound volume data may be prestored in the ultrasound system 300.

The controller 320 may generate an ultrasound volume from ultrasound volume data. The controller 320 may also generate different 3D images according to an orientation in which the same ultrasound volume is viewed. The controller 320 may generate a 3D ultrasound image in a first orientation, i.e., a 3D ultrasound image when an ultrasound volume generated based on ultrasound volume data is viewed in the first orientation. The first orientation may be preset in the ultrasound system 300 or be input by a user.

The display 320 may display a 3D ultrasound image in a first orientation generated by the controller 310.

In addition, the controller 310 may acquire position information and orientation information of an auxiliary display 340 and then determine a second orientation based on the acquired position information and orientation information. It should be noted that acquiring, determining, setting, or using position information and orientation information hereinafter include acquiring, determining, setting or using both or either of the position information and the orientation information. After determining the second orientation, the controller 310 may generate a 3D ultrasound image with the second orientation for an ultrasound volume, i.e., a 3D ultrasound image when the ultrasound volume is viewed in the second orientation, based on the determined second orientation.

The controller 310 may generate an ultrasound volume based on ultrasound volume data, and produce different 3D ultrasound images according to an orientation in which the ultrasound volume is viewed. Referring to FIG. 4, when an ultrasound volume 410 is created based on ultrasound volume data, the controller 310 may generate 3D ultrasound images in different orientations with respect to the ultrasound volume 410. For example, the controller 310 may generate an ultrasound image in a first orientation, i.e., a 3D ultrasound image 420 when the ultrasound volume 410 is viewed from the first orientation, and the display 320 may display the 3D ultrasound image 420 in the first orientation. Furthermore, the controller 310 may generate an ultrasound image in a second orientation, i.e., a 3D ultrasound image 430 when the ultrasound volume 410 is viewed in the second orientation. The controller 310 may also control the auxiliary display 340 to display the 3D ultrasound image 430 with the second orientation. A configuration for controlling the auxiliary display 340 will be described in greater detail below.

In addition, as the position and orientation of the auxiliary display 340 changes, the controller 310 may acquire changed position information and orientation information of the auxiliary display 340 and determine a third orientation based on the changed position information and orientation information.

In detail, the auxiliary display 340 is equipped with a sensor that detects movement and rotation of the auxiliary display 340. According to an exemplary embodiment, the sensor may include at least one selected from a gyro sensor, an accelerometer, and a magnetic sensor, or any other type of sensor that can detect movement or rotation of the auxiliary display 340. The auxiliary display 340 uses the sensor to detect movement of the auxiliary display 340 by a first distance in a first movement direction and rotation thereof by a first angle in a first rotation direction. Based on the result of detection by the sensor, the controller 310 may acquire changed position information and orientation information.

According to an exemplary embodiment, position information and orientation information of the auxiliary display 340 may be initialized. For example, the initialization may be performed by setting the position information and the orientation information to a predefined value. In another exemplary embodiment, the position information and the orientation information of the auxiliary display 340 may be initialized to correspond to a direction (or, orientation) in which the display 320 faces an ultrasound volume at the time of initialization. In this case, at the time of initialization, an orientation of a 3D ultrasound image displayed on the auxiliary display 340 with respect to volume data is the same as that of a 3D ultrasound image displayed on the display 320 with respect to volume data. For example, although the same 3D ultrasound image may be displayed on the display 320 and the auxiliary display 340, a 3D ultrasound image may not necessarily be displayed on the display 320 and the auxiliary display 340 during initialization. According to another exemplary embodiment, the position information and the orientation information of the auxiliary display 340 may be position information and orientation information corresponding to a direction in which the auxiliary display 340 is moved by a certain distance or rotates at a certain angle from a position and an orientation of the display 320 with respect to the ultrasound volume at the time of initialization.

According to an exemplary embodiment, initialization of the position information and orientation information of the auxiliary display 340 may be performed directly by the auxiliary display 340 or according to control by the ultrasound system 300. The initialization may be performed by a user's input of an initialization command to the auxiliary display 340 or the ultrasound system 300, or automatically by the auxiliary display 340 or the ultrasound system 300.

According to an exemplary embodiment, position information and orientation information of the auxiliary display 340 may be preset to predetermined position information and predetermined orientation information, respectively, without being initialized. In this case, for convenience of explanation, the predetermined position information and the predetermined orientation information may be understood as corresponding to initialized position information and initialized orientation information according to an initialization procedure, respectively.

The controller 310 may determine a third orientation based on the changed position information and orientation information and generate a 3D ultrasound image in the determined third orientation. As described above, the third orientation may be determined based on both or one of the changed position information and orientation information. According to an exemplary embodiment, the changed position information and changed orientation information obtained by the controller 310 may include information about the extent or the degree by which a position and an orientation change as compared to the initialized position information and orientation information.

In one exemplary embodiment, when the changed position information indicates that the auxiliary display 340 moves by a first distance in a first movement direction, the controller 310 may control a 3D ultrasound image displayed on the auxiliary display 340 to be moved in a second movement direction and displayed on the auxiliary display 340. For example, the controller 310 may control a 3D ultrasound image displayed on the auxiliary display 340 to be moved in the opposite direction to the first movement direction and displayed on the auxiliary display 340. In this case, the controller 310 may control the 3D ultrasound image to be moved by the same distance as or a distance less than or greater than the first distance before being displayed according to the user's convenience.

According to an exemplary embodiment, when the changed position information indicates that the auxiliary display 340 rotates by a first angle in a first rotation direction, the controller 310 may control a 3D ultrasound image displayed on the auxiliary display 340 to be rotated in a second rotation direction and displayed on the auxiliary display 340. For example, the controller 310 may control a 3D ultrasound image displayed on the auxiliary display 340 to be rotated in the opposite direction to the second rotation direction and displayed on the auxiliary display 340. In this case, the controller 310 may control the 3D ultrasound image to be rotated by the same angle as or an angle less than or greater than the first angle before being displayed according to the user's convenience. Detailed examples of implementation will be described in more detail below.

FIG. 4 illustrates an example of 3D ultrasound images obtained in different orientations with respect to the same ultrasound volume 410.

Referring to FIGS. 3 and 4, when the ultrasound system 300 renders the ultrasound volume 410 for display, a 3D ultrasound image generated when viewed from a first orientation is different from that when viewed from a second orientation. For example, 3D ultrasound images 420 and 430 may be generated when viewed from the first and second orientations, respectively.

In an exemplary embodiment, when the 3D ultrasound image 420 from the first orientation is displayed on the display 320, the 3D ultrasound image 430 may be displayed on the auxiliary display 340. According to an exemplary embodiment, if the auxiliary display 340 moves and rotates, the movement and rotation of the auxiliary display 340 are detected, and an ultrasound image displayed on the auxiliary display 340 is changed according to a direction or extent that the auxiliary display 340 moves and rotates.

Figure 5A:
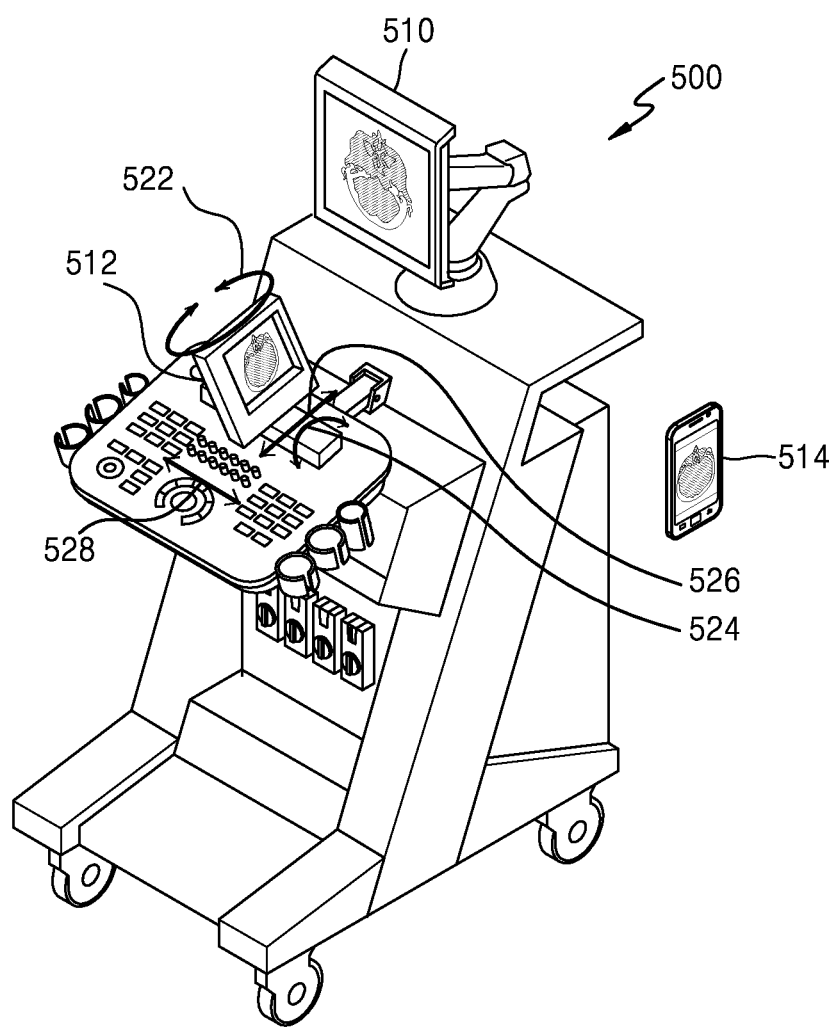

FIGS. 5A and 5B are diagrams illustrating actual implementation of configurations of an ultrasound system 500 according to an exemplary embodiment.

Referring to FIG. 5A, the ultrasound system 500 includes a display 510 that displays a 3D ultrasound image in a first orientation with respect to a specific ultrasound volume. Auxiliary displays may be incorporated into the ultrasound system 500 or implemented in a separate device. In the present exemplary embodiment, an auxiliary display 512 is implemented as a component of the ultrasound system 500 while an auxiliary display 514 is implemented in a device that is separate from the ultrasound system 500. The auxiliary displays 512 and 514 may be movable or rotatable. As the auxiliary displays 512 and 514 move or rotate, the ultrasound system 500 determines a second orientation based on detected position information and orientation information, generates a 3D ultrasound image in a second orientation, and controls the 3D ultrasound image to be displayed on the auxiliary displays 512 and 514. For example, the auxiliary display 512 may move in movement directions 526 and 528 and rotate in rotation directions 522 and 524.

FIG. 5B illustrates a detailed example of implementation of auxiliary displays 562, 564, 566, and 568 in a device separate from an ultrasound system, like implantation of the auxiliary display 514 shown in FIG. 5A. However, the following descriptions with respect to FIG. 5B may be applied to an auxiliary display implemented within an ultrasound system, like the auxiliary display 512.

Referring to FIG. 5B, a display 560 displays a 3D ultrasound image in a first orientation with respect to volume data. For example, the first orientation may be a direction that the volume data is viewed from the front. 3D ultrasound images in various orientations may be displayed on the auxiliary displays 562, 564, 566, and 568 according to a position and an orientation of the device including the auxiliary displays 562, 564, 566, and 568.

For example, the auxiliary display 564 may be built into a front surface of a smartphone. If the smartphone including the auxiliary display 564 is located on the right side of the display 550 and rotates so that a rear surface thereof faces the display 560, a 3D ultrasound image generated when volume data is viewed from the right side may be displayed on the auxiliary display 564. As another example, if a smartphone having the auxiliary display 566 built into a front surface thereof is located on top of the display 560 and rotates so that a rear surface thereof faces the display 560, a 3D ultrasound image generated when volume data is viewed from the top may be displayed on the auxiliary display 566. Similarly, 3D ultrasound images generated when volume data is viewed from the front side and the left side may be displayed on the auxiliary displays 562 and 568, respectively. In this case, the device including the auxiliary displays 562, 564, 566, and 568 may be realized as a mobile phone, a tablet PC, and an auxiliary monitor as well as a smartphone.

The above-described exemplary embodiments may be understood intuitively by referring to a 3D shape 570 shown in FIG. 5B. If it is assumed that the 3D shape 570 is ultrasound volume data, and that a 3D ultrasound image in a first orientation is an image indicating a view from the front side with respect to the ultrasound volume, the 3D ultrasound image displayed on the display 560 may correspond to a front view 582. Similarly, the 3D ultrasound images displayed on the auxiliary displays 564, 566, and 568 may correspond to a right side view 584, a plan view 586, and a left side view 588, respectively.

In another exemplary embodiment, if the auxiliary display 562, 564, 566, and 568 are built into front surfaces of smartphones and rotate so that the front surfaces thereof face the display 560, 3D ultrasound images generated when an ultrasound volume is reflected from the auxiliary displays 562, 564, 566, and 568 that function as mirrors may be displayed on the auxiliary displays 562, 564, 566, and 568. According to the exemplary embodiment, an ultrasound system may initialize position information and orientation information of the auxiliary display 562, 564, 566, or 568 by placing the auxiliary display 562, 564, 566, or 568 near a front or rear surface of the display 560, and then generate a 3D image that is displayed on the auxiliary display 562, 564, 566, or 568 according to a change in position information and orientation information thereof.

In the previous exemplary embodiment, it has been described that the smartphones including the auxiliary displays 562, 564, 566, and 568 rotate so that rear surfaces thereof face the display 560 by moving to the right side, left side, and top of the display 560. However, according to exemplary embodiments, the auxiliary displays 562, 564, 566, and 568 may display images generated when volume data is viewed from the front, the right side, the left side, and the top, respectively, only by rotating while remaining stationary (or regardless of a change in position). In the same manner, the auxiliary display 512 of the ultrasound system 500 may display images generated when volume data is viewed from the right side, the left side, and the top only by rotating in the rotation directions 522 and 524 without moving in the movement directions 526 and 528. In this case, the ultrasound system 500 may display 3D ultrasound images in different orientations by using only orientation information without using position information of the auxiliary display 514 or without regard to the position information thereof.

Furthermore, according to an exemplary embodiment, 3D ultrasound images displayed on the auxiliary displays 562, 564, 566, and 568 may be further enlarged as the auxiliary displays 562, 564, 566, and 568 move closer to the display 560. In another exemplary embodiment, 3D ultrasound images displayed on the auxiliary displays 562, 564, 566, and 568 may be further enlarged as the auxiliary displays 562, 564, 566, and 568 move closer to a predetermined reference position other than the display 560.

Thus, according to exemplary embodiments, a user may intuitively set an orientation in which he or she desires to view volume data, and view a 3D ultrasound image corresponding to the orientation via an auxiliary display.

Figure 6A:
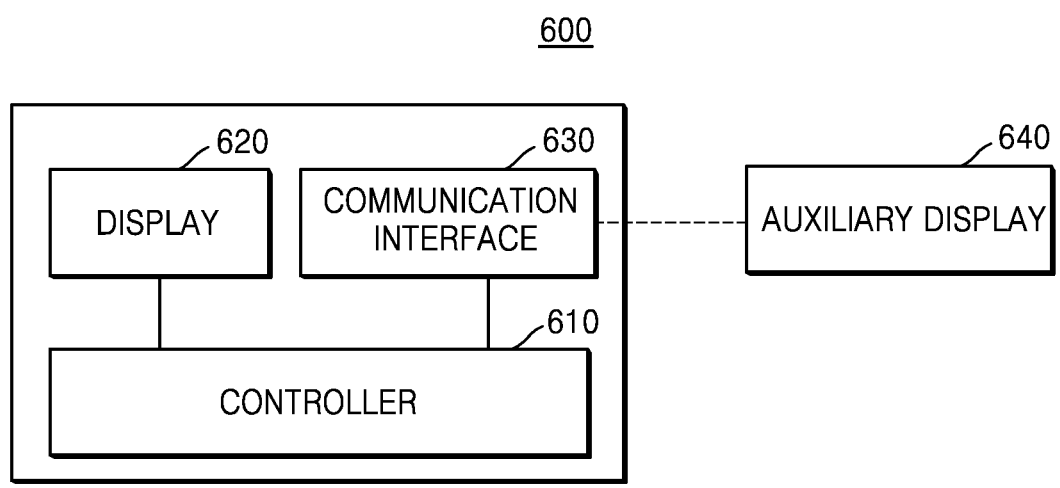
FIGS. 6A and 6B are diagrams of ultrasound systems according to other exemplary embodiments.
Figure 6B:
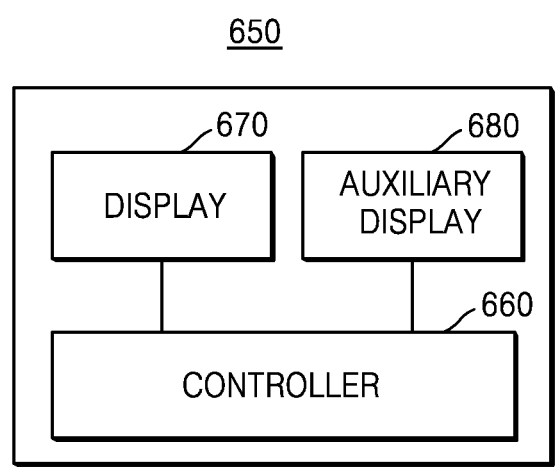

FIGS. 6A and 6B are diagrams of ultrasound systems 600 and 650 according to other exemplary embodiments.

Referring to FIG. 6A, the ultrasound system 600 according to another exemplary embodiment includes a controller 610, a display 620, and a communication interface 630. An auxiliary display 640 may be implemented separately in an external device.

The ultrasound system 600 communicates with the external device including the auxiliary display 640 via the communication interface 630. The communication interface 630 may perform communication by wire or wirelessly, i.e., by using any type of wired or wireless communication technologies including Bluetooth, Wi-Fi, and 3G.

The communication interface 630 receives position information and orientation information of the auxiliary display 640 from the external device including the auxiliary display 640. Furthermore, when the controller 610 determines a second orientation corresponding to the position information and orientation information of the auxiliary display 640 and generates a 3D ultrasound image in the second orientation with respect to ultrasound volume data, the communication interface 630 then transmits the 3D ultrasound image to the auxiliary display 640. According to an exemplary embodiment, the communication interface 630 may transmit a command signal that initializes position information and orientation information of the auxiliary display 640 to the auxiliary display 640, and receive initialized position information and orientation information from the auxiliary display 640.

Since other configurations or functions of the controller 610, the display 620, and the auxiliary display 640 are the same as described above, detailed descriptions thereof are omitted.

Referring to FIG. 6B, the ultrasound system 650 according to the present exemplary embodiment includes an auxiliary display 680. The ultrasound system 650 has a similar configuration to that of the ultrasound system 500 of FIG. 5 including the auxiliary display 512.

In this case, position information and orientation information of the auxiliary display 680 may be acquired directly by a controller 660. Since other configurations or functions of the controller 660, the display 670, and the auxiliary display 680 are the same as described above, detailed descriptions thereof are omitted.

Figure 7:
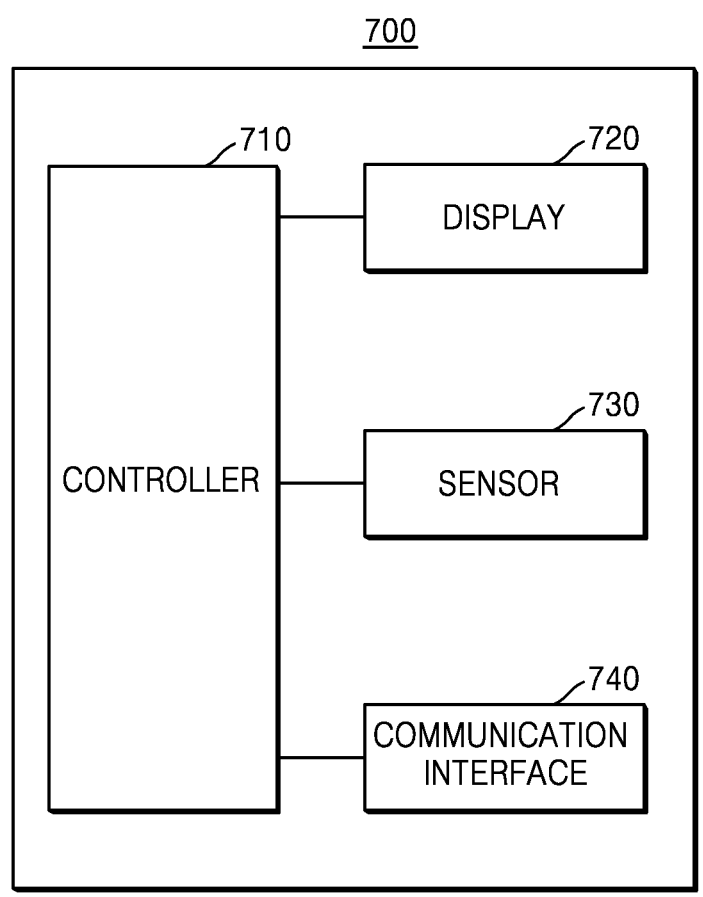
FIG. 7 is a diagram of an image display device including an auxiliary display, according to an exemplary embodiment.

FIG. 7 is a diagram of an image display device 700 including an auxiliary display. The image display device 700 may include a sensor 730, a controller 710, and a display 720. As compared to FIG. 5A, the display 720 may correspond to the auxiliary display 514, and the image display device 700 may correspond to an external device including the auxiliary display 514, such as a mobile phone, a smartphone, a tablet PC, or an auxiliary monitor.

When the image display device 700 moves or rotates, the sensor 730 may detect a direction and a distance of movement or a direction and an angle of rotation. To do so, the sensor 730 may include at least one selected from a gyro sensor, an accelerometer, and a magnetic sensor. However, the sensor 730 may include any type of sensor capable of detecting a position and an orientation of the image display device 700.

The controller 710 generates position information and orientation information based on the result of detection by the sensor 730. The communication interface 740 transmits the position information and the orientation information generated by the controller 710 to an external device, e.g., the ultrasound system 500 of FIG. 5A.

The communication interface 740 also receives a 3D ultrasound image corresponding to the transmitted position information and the orientation information from the external device. The display 720 displays the 3D ultrasound image received by the communication interface 740.

The sensor 730 detects a position and an orientation of the image display device 700, the communication interface 740 transmits the position information and the orientation information to the outside and receives a 3D ultrasound image from the outside, and the display 720 displays the received 3D ultrasound image. The whole procedure may be performed iteratively, periodically, or in real-time.

As described above, the image display device 700 may initialize the position information and the orientation information thereof. The initialization may be performed by receiving an initialization command from a user or the communication interface 740.

Figure 8:
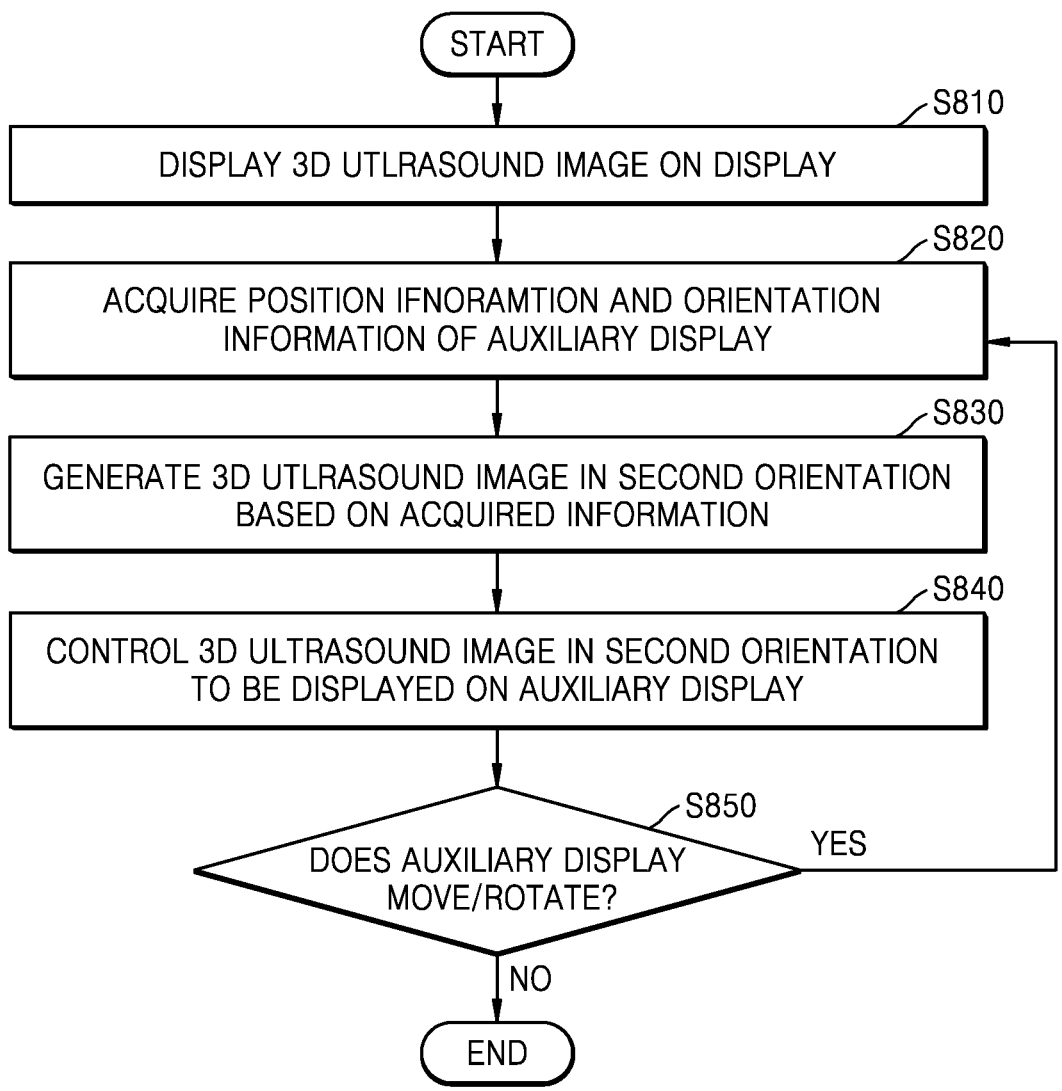
FIG. 8 is a flowchart of a method of displaying 3D ultrasound images on a display and an auxiliary display of an ultrasound system, according to an exemplary embodiment.

FIG. 8 is a flowchart of a method of displaying 3D ultrasound images on a display and an auxiliary display of an ultrasound system, according to an exemplary embodiment Referring to FIG. 8, a 3D ultrasound image in a first orientation with respect to an ultrasound volume is displayed on the display of the ultrasound system (S810).

The ultrasound system acquires position information and orientation information of the auxiliary display (S820).

The ultrasound system produces a 3D ultrasound image in a second orientation with respect to the ultrasound volume based on the acquired position information and orientation information (S830).

The ultrasound system controls the 3D ultrasound image in the second orientation to be displayed on the auxiliary display (S840).

It is determined whether the auxiliary display moves or rotates (S850). According to an exemplary embodiment, if the auxiliary display is included in the ultrasound system, the ultrasound system detects whether the auxiliary display moves or rotates. In another exemplary embodiment, if the auxiliary display is not included in the ultrasound system, an external image display device including the auxiliary display may detect movement or rotation of the external image display device or the auxiliary display and then transmit position information and orientation information generated as a result of the detection to the ultrasound system.

If a position and an orientation of the auxiliary display are not determined to be changed in operation S850, the 3D ultrasound image in the second orientation remains as it is displayed on the auxiliary display. On the other hand, if the position and the orientation of the auxiliary display are determined to be changed, the process returns to operation S820. The ultrasound system acquires position information and orientation information of the auxiliary display and iteratively performs operations S830, S840, and S850.

Figure 9:
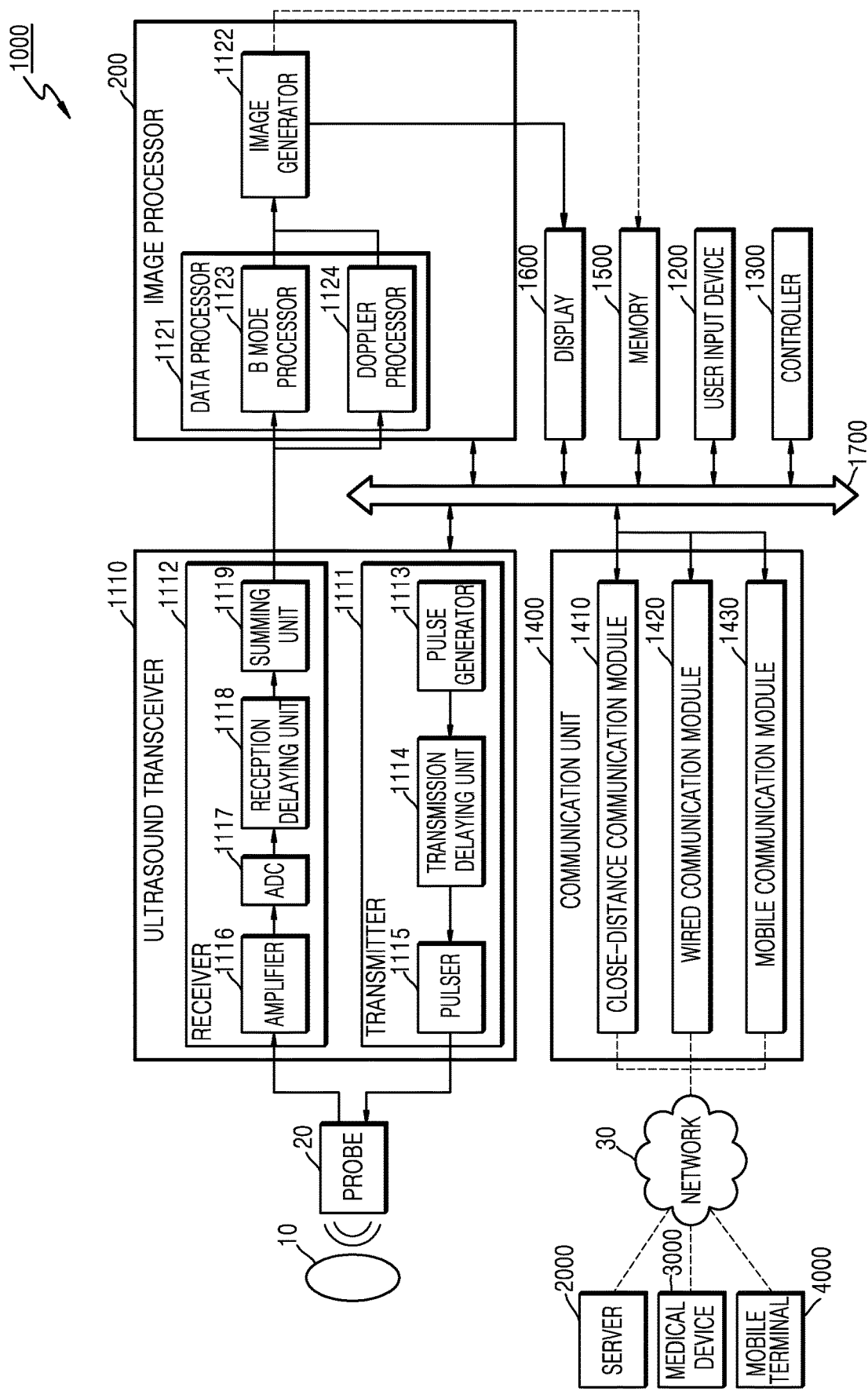
FIG. 9 is a block diagram of an ultrasound diagnosis apparatus to which an ultrasound system according to an exemplary embodiment may be applied.

FIG. 9 is a block diagram of an ultrasound diagnosis apparatus 1000 to which the ultrasound system 300 according to an embodiment may be applied.

A method of editing an ultrasound image, according to an embodiment, may be performed by the ultrasound diagnosis apparatus 1000 of FIG. 9, and the ultrasound system 300 according to an embodiment may be included in the ultrasound diagnosis apparatus 1000 of FIG. 9.

The ultrasound system 300 of FIG. 3 may perform some or all functions performed by the ultrasound diagnosis apparatus 1000 of FIG. 9. The display 320 of FIG. 3 may correspond to a display unit 1600 of FIG. 9, and the controller 310 of FIG. 3 may include some or perform some functions of an ultrasound transceiver 1110, an image processor 1120, a communication unit 1400, and a controller 1300 of FIG. 9. Also, communication interface 630 of FIG. 6a may correspond to communication unit 1400 of FIG. 9.

The components of the ultrasound diagnosis apparatus 1000 of FIG. 9 will be described below.

An ultrasound image data acquiring unit 1100 according to an embodiment may obtain ultrasound image data of an object 10. The ultrasound image data according to an embodiment may be 2D ultrasound image data or 3D ultrasound image data of the object 10.

According to an embodiment, the ultrasound image data acquiring unit 1100 may include a probe 20, the ultrasound transceiver 1110, and the image processor 1120.

The probe 20 transmits ultrasound signals to the object 10 according to a driving signal applied by the ultrasound transceiver 1110 and receives ultrasound echo signals reflected by the object 10. The probe 20 includes a plurality of transducers, and the plurality of transducers oscillate in response to electric signals and generate acoustic energy, that is, ultrasound waves. Furthermore, the probe 20 may be connected to the main body of the ultrasound diagnosis apparatus 1000 by wire or wirelessly. According to the embodiments of the present inventive concept, the ultrasound diagnosis apparatus 1000 may include a plurality of probes 20. According to an embodiment, the probe 20 may include at least one selected from a 1-dimensional (1D) probe, a 1.5-dimensional probe, a 2D (matrix) probe, and a 3D probe.

A transmitter 1111 supplies a driving signal to the probe 20. The transmitter 1111 includes a pulse generator 1113, a transmission delaying unit 1114, and a pulser 1115. The pulse generator 1113 generates pulses for forming transmission ultrasound waves based on a predetermined pulse repetition frequency (PRF), and the transmission delaying unit 1114 delays the pulses by delay times necessary for determining transmission directionality. The pulses, which have been delayed, correspond to a plurality of piezoelectric vibrators included in the probe 20, respectively. The pulser 1115 applies a driving signal (or a driving pulse) to the probe 20 based on timing corresponding to each of the pulses, which have been delayed.

A receiver 1112 generates ultrasound data by processing echo signals received from the probe 20. The receiver 1112 may include an amplifier 1116, an analog-to-digital converter (ADC) 1117, a reception delaying unit 1118, and a summing unit 1119. The amplifier 1116 amplifies echo signals in each channel, and the ADC 1117 performs analog-to-digital conversion on the each of the amplified signals. The reception delaying unit 1118 delays digital echo signals output by the ADC 1117 by delay times necessary for determining reception directionality, and the summing unit 1119 generates ultrasound data by summing the echo signals processed by the reception delaying unit 1118. For example, the summing unit 1119 may generate shoulder ultrasound image data. Alternatively, the summing unit 1119 may obtain shoulder ultrasound image data in real-time while a drug is injected into a bursa through a needle.

The image processor 1120 generates an ultrasound image by scan-converting ultrasound image data generated by the ultrasound transceiver 1110. The ultrasound image may be not only a grayscale ultrasound image obtained by scanning an object in an amplitude (A) mode, a brightness (B) mode, and a motion (M) mode, but also a Doppler image showing movements of an object via a Doppler effect. The Doppler image may be a blood flow Doppler image showing flow of blood (also referred to as a color Doppler image), a tissue Doppler image showing movements of tissue, or a spectral Doppler image showing a moving speed of an object as a waveform.

A B mode processor 1123 extracts B mode components from ultrasound image data and processes the B mode components. An image generator 1122 may generate a B mode image indicating signal intensities as brightness based on the B mode components extracted by the B mode processor 1123. For example, the image generator 1122 may generate a shoulder ultrasound image, including a deltoid, fat layers, bursae, and tendons, as a 2D B mode image.

The image generator 1122 may sequentially generate a plurality of B mode images. For example, the image generator 1122 may generate a first B mode image and a second B mode image. Alternatively, the image generator 1122 may generate a shoulder ultrasound image in real-time while a drug is injected into a bursa through a needle.

A Doppler processor 1124 may extract Doppler components from ultrasound image data, and the image generator 1122 may generate a Doppler image indicating movements of an object as colors or waveforms based on the extracted Doppler components.

According to an embodiment, the image generator 1122 may generate a 3D ultrasound image via volume-rendering with respect to volume data and may also generate an elasticity image by imaging the deformation of the object 10 due to pressure. Furthermore, the image generator 1122 may generate a speckle detection image by estimating moving paths of speckles from the ultrasound image data and indicating movements of the speckles as arrows or colors based on the estimated moving paths.

Furthermore, the image generator 1122 may display various pieces of additional information on an ultrasound image by using text and graphics. For example, the image generator 1122 may add at least one annotation related to all or some portions of the ultrasound image to the ultrasound image. That is, the image generator 1122 may analyze the ultrasound image and recommend at least one annotation related to all or some portions of the ultrasound image based on the analysis result. Alternatively, the image generator 1122 may add at least one annotation selected by the user to the ultrasound image.

The image processor 1120 may extract an interest region from the ultrasound image by using an image processing algorithm. In this case, the image processor 1120 may add colors, patterns, or boundaries to the interest region.

The user input device 1200 is a means via which a user (for example, a sonographer) inputs data for controlling the ultrasound diagnosis apparatus 1000. For example, the user input device 1200 may include a keypad, a dome switch, a touchpad (a capacitive overlay type, a resistive overlay type, an infrared beam type, an integral strain gauge type, a surface acoustic wave type, a piezoelectric type, etc.), a trackball, and a jog switch. However, embodiments of the present inventive concept are not limited thereto, and the user input device 1200 may further include any one of various other input units including an electrocardiogram (ECG) measuring module, a respiration measuring module, a voice recognition sensor, a gesture recognition sensor, a fingerprint recognition sensor, an iris recognition sensor, a depth sensor, a distance sensor, etc.

According to an embodiment, the user input device 1200 may detect not only a real-touch but also a proximity touch. The user input device 1200 may detect a touch input (for example, touch and holding, tapping, double tapping, or flicking) on an ultrasound image. Also, the user input device 1200 may detect a drag input from a point where a touch input is detected. The user input device 1200 may detect a multi-touch input (for example, pinching) on at least two points in the ultrasound image.

According to an embodiment, the user input device 1200 may receive an input for selecting an interest region in a B mode image. For example, the user input device 1200 may receive a user input for selecting an interest region, including a deltoid and tendons, in a shoulder ultrasound image.

The controller 1300 may control all operations of the ultrasound diagnosis apparatus 1000. For example, the controller 1300 may control operations of the ultrasound image data acquiring unit 1100, the user input device 1200, the communication unit 1400, a memory 1500, and the display unit 1600.

The controller 1300 may detect a fat layer located between a deltoid and tendons based on echo signal intensity information included in shoulder ultrasound image data.

For example, the controller 1300 may detect a region of which intensities of echo signals are greater than a threshold value as a fat layer. Also, in the shoulder ultrasound image, the controller 1300 may determine a first boundary of which an intensity changing degree of echo signals is greater than a positive first threshold value as an upper portion of the fat layer and a second boundary of which an intensity changing degree of echo signals is less than a negative second threshold value as a lower portion of the fat layer. Also, the controller 1300 may detect a thickness of the fat layer based on a distance between the first and second boundaries.

The controller 1300 may detect a bursa located between the fat layer and the tendons by using a location of the fat layer. For example, the controller 1300 may determine an anechoic zone under the fat layer as the bursa.

Also, in the shoulder ultrasound image, the controller 1300 may extract a third boundary of which an intensity changing degree of echo signals is less than the first threshold value but greater than a third threshold value, and determine the third boundary as an upper portion of the tendons. In addition, the controller 1300 may detect a thickness of the bursa based on a distance between the second and third boundaries.

When an interest region is selected, the controller 1300 may detect the fat layer based on echo signal intensity information of the interest region. Also, the controller 1300 may change a location or a size of the interest region based on a location of the fat layer or a location of the bursa.

The communication unit 1400 may include at least one component for allowing communication between the ultrasound diagnosis apparatus 1000 and a server 2000, the ultrasound diagnosis apparatus 1000 and a medical device 3000, and the ultrasound diagnosis apparatus 1000 and a mobile terminal 4000. For example, the communication unit 1400 may include a close-distance communication module 1410, a wired communication module 1420, and a mobile communication module 1430.

The close-distance communication module 1410 refers to a module for close-distance communication within a predetermined distance. Examples of close-distance communication technologies may include Wi-Fi, Bluetooth, Bluetooth low energy (BLE), ultra wideband (UWB), ZigBee, near field communication (NFC), Wi-Fi Direct (WFD), and infrared data association (IrDA).

The wired communication module 1420 refers to a module for communication using electric signals or optical signals. Examples of wired communication technologies according to an embodiment may include communication via a pair cable, a coaxial cable, an optical fiber cable, and an Ethernet cable.

The mobile communication module 1430 transmits or receives wireless signals to at least one selected from a base station, an external device (3000, 4000), or the server 2000 on a mobile communication network. The wireless signals may be voice call signals, video call signals, or various types of data for transmission and reception of text/multimedia messages.

The communication unit 1400 may be connected to a network 30 by wire or wirelessly to communicate with an external device (for example, the medical device 3000 or the mobile terminal 4000) or the server 2000. The communication unit 1400 may exchange data with a hospital server or another medical apparatus in a hospital, which is connected thereto via a picture archiving and communication system (PACS). Furthermore, the communication unit 1400 may perform data communication according to the digital imaging and communications in medicine (DICOM) standard.

The communication unit 1400 may transmit or receive data related to diagnosis of the object 10, e.g., an ultrasound image, ultrasound image data, and Doppler data of the object 10, via the network 30 and may also transmit or receive medical images captured by another medical apparatus, e.g., a computed tomography (CT) apparatus, a magnetic resonance imaging (MRI) apparatus, or an X-ray apparatus. Furthermore, the communication unit 1400 may receive information about a diagnosis history or medical treatment schedule of a patient from the server 2000 and utilize the received information for the diagnosis of the object 10.

The memory 1500 may store a program for processing the controller 1300 or data that is input or output (for example, ultrasound image data, information about a drug spreading boundary, information of a subject to be tested, probe information, or a body marker).

The memory 1500 may include at least one type of storage medium selected from a flash memory, a hard disk drive, a multimedia card micro type memory, a card type memory (for example, a secure digital (SD) or an XD memory), random access memory (RAM), static RAM (SRAM), read-only memory (ROM), electrically erasable programmable ROM (EEPROM), programmable ROM (PROM), a magnetic memory, a magnetic disc, and an optical disc. Also, the ultrasound diagnosis apparatus 1000 may manage a web storage or a cloud server that performs as a storage like the memory 1500 on the Internet.

The display unit 1600 displays information processed by the ultrasound diagnosis apparatus 1000. For example, the display unit 1600 may display an ultrasound image or a user interface (UI) or a graphical UI (GUI) related to a control panel.

According to an embodiment, the display unit 1600 may display location information of a bursa on a shoulder ultrasound image generated based on shoulder ultrasound image data. For example, the display unit 1600 may display a preset indicator at a location of the bursa on the shoulder ultrasound image. The display unit 1600 may display a first boundary line that distinguishes the bursa from a fat layer and a second boundary line that distinguishes the bursa from tendons.

When the display unit 1600 and a touch pad are layered and thus provided as a touch screen, the display unit 1600 may be used as not only an output device but also as an input device. The display unit 1600 may include at least one selected from a liquid crystal display (LCD), a thin film transistor LCD, an organic light-emitting diode display, a flexible display, a 3D display, and an electrophoretic display. Also, according to the embodiments of the present inventive concept, the number of display units 1600 included in the ultrasound diagnosis apparatus 1000 may be two or more.

A method according to exemplary embodiments may be implemented through program instructions that are executable via various computer devices and recorded in computer-readable recording media. The computer-readable recording media may include program instructions, data files, data structures, or a combination thereof. The program instructions may be specifically designed for the present inventive concept or well-known to one of ordinary skill in the art of computer software. Examples of the computer-readable recording media include magnetic media (e.g., hard disks, floppy disks, or magnetic tapes), optical media (e.g., CD-ROMs or DVDs), magneto-optical media (e.g., floptical disks), and hardware devices specifically designed to store and execute the program instructions (e.g., ROM or RAM). Examples of the program instructions not only include machine codes that are made by compilers but also computer-executable high level language codes that may be executed by using an interpreter.

As described above, according to the one or more of the above exemplary embodiments, labels may be more accurately and conveniently edited with regard to geometric shapes of labels generated on a 3D ultrasound image.

While one or more exemplary embodiments have been described with reference to the figures, it will be understood by those of ordinary skill in the art that various changes in form and details may be made therein without departing from the spirit and scope as defined by the following claims.

What is claimed is:

1. An ultrasound system comprising:
a display; and
a controller configured to generate, from ultrasound volume data acquired from an object, a three-dimensional (3D) ultrasound image,
wherein the controller is further configured to:
acquire first position information and first orientation information of the display,
control the display to display the generated 3D ultrasound image in a first orientation based on the first orientation information,
acquire second position information and second orientation information of an auxiliary display,
identify a second orientation with respect to the generated 3D ultrasound image based on a first difference between the first orientation information and the second orientation information, and
control the auxiliary display to display the generated 3D ultrasound image in the second orientation with a changed size based on a second difference between the first position information and the second position information.

2. The ultrasound system of claim 1, wherein the controller acquires at least one from among third position information and third orientation information of the auxiliary display, identifies a third orientation with respect to the generated 3D ultrasound image based on at least one of a third difference between the second orientation information and the third orientation information and a fourth difference between the second position information and the third position information, and controls the auxiliary display to display the generated 3D ultrasound image in the third orientation.

3. The ultrasound system of claim 2, wherein the controller initializes the at least one from among the second position information and the second orientation information of the auxiliary display.

4. The ultrasound system of claim 3, wherein the controller compares the at least one from among the third position information and the third orientation information with at least one from among the initialized second position information and the initialized second orientation information, and control the auxiliary display to display the 3D ultrasound image in the third orientation according to a comparison result.

5. The ultrasound system of claim 2, wherein when the third orientation information indicates that the auxiliary display rotates in a first rotation direction, the controller controls the 3D ultrasound image in the second orientation displayed on the auxiliary display to be rotated in a second rotation direction and be displayed on the auxiliary display.

6. The ultrasound system of claim 1, further comprising the auxiliary display implemented in an image displaying device separated from the ultrasound system.

7. The ultrasound system of claim 6, further comprising a communication interface for receiving the at least one from among the second position information and the second orientation information from the auxiliary display,
wherein the controller controls the communication interface to transmit the 3D ultrasound image in the second orientation generated based on the received at least one from among the second position information and the second orientation information to the auxiliary display.

8. An image displaying device for displaying an ultrasound image, the image displaying device comprising:
a communication interface configured to receive first ultrasound image data from an ultrasound system, the ultrasound system configured to acquire ultrasound volume data;
a display configured to display a three-dimensional (3D) ultrasound image in a first orientation using the first ultrasound image data, based on at least one from among position information and orientation information of the image displaying device;
a sensor configured to detect a change in at least one from among a position and an orientation of the image displaying device; and
a controller configured to:
control the communication interface to transmit at least one from among changed position information and changed orientation information of the image displaying device according to a detection result to the ultrasound system;
control the communication interface to receive second ultrasound image data from the ultrasound system; and
control the display to display the 3D ultrasound image in a second orientation with a changed size based on the changed position information using the second ultrasound image data,
wherein the second ultrasound image data is generated based on the changed position information and the changed orientation information of the image displaying device.

9. The image displaying device of claim 8, wherein the sensor includes at least one from among a gyro sensor, an accelerometer, and a magnetic sensor.

10. The image displaying device of claim 8, wherein the communication interface communicates with the ultrasound system via at least one from among wireless and wired communication channels, and
wherein the image displaying device is at least one from among a mobile phone, a smartphone, a tablet PC, an auxiliary monitor, and a portable computer.

11. The image displaying device of claim 8, wherein the controller initializes the at least one from among the position information and the orientation information of the image displaying device according to a command that initializes the at least one from among the position information and the orientation information thereof, and
wherein the communication interface transmits the initialized at least one from among the position information and the orientation information to the ultrasound system.

12. The image displaying device of claim 8, wherein when the changed orientation information indicates that the image displaying device rotates in a first rotation direction, the 3D ultrasound image in the second orientation is a 3D ultrasound image displayed by rotating the 3D ultrasound image with the first orientation in a second rotation direction.

13. A method of displaying an image in an ultrasound system, the method comprising:
generating, from ultrasound volume data acquired from an object, a three-dimensional (3D) ultrasound image;
acquiring first position information and first orientation information of a display;
displaying the generated 3D ultrasound image in a first orientation on the display based on the first orientation information;
acquiring second position information and second orientation information of an auxiliary display;
identifying a second orientation with respect to the generated 3D ultrasound image based on a first difference between the first orientation information and the second orientation information; and
controlling the auxiliary display to display the generated 3D ultrasound image in the second orientation with a changed size based on a second difference between the first position information and the second position information.

14. The method of claim 13, further comprising:
acquiring at least one from among third position information and third orientation information of the auxiliary display and identifying a third orientation with respect to the generated 3D ultrasound image based on at least one of a third difference between the second orientation information and the third orientation information and a fourth difference between the second position information and the third position information; and
controlling the auxiliary display to display the generated 3D ultrasound image in the third orientation.

15. The method of claim 14, further comprising initializing the at least one from among the second position information and the second orientation information of the auxiliary display.

16. The method of claim 15, further comprising:
comparing the at least one from among the third position information and the third orientation information with at least one from among the initialized second position information and the initialized second orientation information; and
controlling the auxiliary display to display the 3D ultrasound image in the third orientation according to a comparison result.

17. The method of claim 14, wherein when the third orientation information indicates that the auxiliary display rotates in a first rotation direction, the 3D ultrasound image in the second orientation displayed on the auxiliary display is rotated in a second rotation direction and is displayed on the auxiliary display.

18. The method of claim 13, further comprising:
receiving the at least one from among the second position information and the second orientation information from the auxiliary display; and
transmitting the 3D ultrasound image in the second orientation generated based on the received at least one from among the second position information and the second orientation information to the auxiliary display.

19. A non-transitory computer-readable recording medium having recorded thereon a program for executing the method of claim 13 on a computer.

20. A method of displaying an image in an image displaying device, the method comprising:

receiving first ultrasound image data from an ultrasound system, the ultrasound system configured to acquire ultrasound volume data;

displaying, on a display of the image displaying device, a three-dimensional (3D) ultrasound image in a first orientation using the first ultrasound image data, wherein the first orientation is determined based on at least one from among position information and orientation information of the image displaying device;

detecting a change in at least one from among a position and an orientation of the image displaying device;

transmitting at least one from among changed position information and changed orientation information of the image displaying device according to a detection result to the ultrasound system;

receiving second ultrasound image data from the ultrasound system; and displaying, on the display of the image displaying device, the 3D ultrasound image in a second orientation with a changed size based on the changed position information using the second ultrasound image data, wherein the second ultrasound image data is generated based on the changed position information and the changed orientation information of the image displaying device.

21. The method of claim 20, wherein the detecting of the change is performed by using at least one from among a gyro sensor, an accelerometer, and a magnetic sensor.

22. The method of claim 20, wherein the image displaying device is at least one from among a mobile phone, a smartphone, a tablet PC, an auxiliary monitor, and a portable computer, all of which include a communication interface, and the transmitting of the determined at least one from among the changed position information and the changed orientation information and the receiving of the 3D ultrasound image are performed using the communication interface.

23. The method of claim 20, further comprising:

initializing the at least one from among the position information and the orientation information of the image displaying device according to a command that initializes the at least one from among the position information and the orientation information thereof; and transmitting the initialized at least one from among the position information and the orientation information to the ultrasound system.

24. The method of claim 20, wherein when the changed orientation information indicates that the image displaying device rotates in a first rotation direction, the 3D ultrasound image in the second orientation is a 3D ultrasound image displayed by rotating the 3D ultrasound image with the first orientation in a second rotation direction.

* * * * *